United States Patent
Dong et al.

(10) Patent No.: US 8,078,276 B2
(45) Date of Patent: *Dec. 13, 2011

(54) ELECTROGRAM MORPHOLOGY-BASED CRT OPTIMIZATION

(75) Inventors: Yanting Dong, Shoreview, MN (US); Jiang Ding, Shoreview, MN (US); Douglas R. Daum, Woodbury, MN (US); Scott A. Meyer, Lakeville, MN (US); Yinghong Yu, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 226 days.

This patent is subject to a terminal disclaimer.

(21) Appl. No.: 12/494,628

(22) Filed: Jun. 30, 2009

(65) Prior Publication Data

US 2009/0264949 A1    Oct. 22, 2009

Related U.S. Application Data

(63) Continuation of application No. 11/097,460, filed on Apr. 1, 2005, now Pat. No. 7,555,340.

(51) Int. Cl.
*A61N 1/365* (2006.01)

(52) U.S. Cl. .......................................... 607/9

(58) Field of Classification Search .............. 607/9, 11, 607/14, 17, 18, 23–25, 27, 28, 30; 600/508–510, 600/515, 516, 518
See application file for complete search history.

(56) References Cited

U.S. PATENT DOCUMENTS

| | | | |
|---|---|---|---|
| 4,832,041 A | 5/1989 | Wang et al. | |
| 4,895,152 A | 1/1990 | Callaghan et al. | |
| 5,273,049 A | 12/1993 | Steinhaus et al. | |
| 5,312,445 A | 5/1994 | Nappholz et al. | |
| 5,330,511 A | 7/1994 | Boute | |
| 5,331,966 A | 7/1994 | Bennett et al. | |
| 5,334,220 A | 8/1994 | Sholder | |
| 5,340,361 A | 8/1994 | Sholder | |
| 5,350,410 A | 9/1994 | Kleks et al. | |
| 5,391,192 A | 2/1995 | Lu et al. | |
| 5,431,691 A | 7/1995 | Snell et al. | |
| 5,458,623 A | 10/1995 | Lu et al. | |
| 5,534,016 A | 7/1996 | Boute | |
| 5,540,727 A | 7/1996 | Tockman et al. | |
| 5,626,623 A | 5/1997 | Kieval et al. | |
| 5,660,184 A | 8/1997 | Donehoo et al. | |
| 5,674,254 A | 10/1997 | van Krieken | |

(Continued)

FOREIGN PATENT DOCUMENTS

EP        1123716        8/2001

(Continued)

OTHER PUBLICATIONS

"U.S. Appl. No. 11/620,901, Restriction Requirement mailed Nov. 27, 2009", 5 pgs.

(Continued)

*Primary Examiner* — Carl H Layno
*Assistant Examiner* — Jessica Sarcione
(74) *Attorney, Agent, or Firm* — Schwegman, Lundberg & Woessner, P.A.

(57) ABSTRACT

A method and system for determining an optimum atrioventricular delay (AVD) interval and/or ventriculo-ventricular delay (VVD) intervals for delivering ventricular resynchronization pacing in an atrial tracking or atrial sequential pacing mode. Evoked response electrograms recorded at different AVD and VVD intervals are used to determine the extent of paced and intrinsic activation.

20 Claims, 3 Drawing Sheets

U.S. PATENT DOCUMENTS

| | | | |
|---|---|---|---|
| 5,741,308 | A | 4/1998 | Sholder |
| 5,755,739 | A | 5/1998 | Sun et al. |
| 5,771,898 | A | 6/1998 | Marinello |
| 5,778,881 | A | 7/1998 | Sun et al. |
| 5,782,888 | A | 7/1998 | Sun et al. |
| 5,817,134 | A | 10/1998 | Greenhut |
| 5,830,150 | A | 11/1998 | Palmer et al. |
| 6,029,088 | A | 2/2000 | Budgifvars et al. |
| 6,101,416 | A | 8/2000 | Sloman |
| 6,128,535 | A | 10/2000 | Maarse |
| 6,169,921 | B1 | 1/2001 | KenKnight et al. |
| 6,253,102 | B1 | 6/2001 | Hsu et al. |
| 6,304,773 | B1 | 10/2001 | Taylor et al. |
| 6,418,340 | B1 | 7/2002 | Conley et al. |
| 6,456,881 | B1 | 9/2002 | Bornzin |
| 6,512,953 | B2 | 1/2003 | Florio et al. |
| 6,556,866 | B2 | 4/2003 | Dal Molin et al. |
| 6,597,951 | B2 | 7/2003 | Kramer et al. |
| 6,609,023 | B1 | 8/2003 | Fischell et al. |
| 6,622,040 | B2 | 9/2003 | Ding et al. |
| 6,697,673 | B1 | 2/2004 | Lu |
| 6,738,669 | B1 | 5/2004 | Sloman et al. |
| 6,748,274 | B2 | 6/2004 | Levine et al. |
| 6,829,505 | B2 | 12/2004 | Kramer et al. |
| 6,832,112 | B1 | 12/2004 | Bornzin |
| 6,865,422 | B1 | 3/2005 | Sloman et al. |
| 6,904,321 | B1 | 6/2005 | Bornzin et al. |
| 7,113,823 | B2 | 9/2006 | Yonce et al. |
| 7,177,689 | B2 | 2/2007 | Ternes et al. |
| 7,181,284 | B2 | 2/2007 | Burnes |
| 7,203,543 | B2 | 4/2007 | Meyer et al. |
| 7,286,876 | B2 | 10/2007 | Yonce et al. |
| 7,353,061 | B2 | 4/2008 | Hedberg et al. |
| 7,412,287 | B2 | 8/2008 | Yonce et al. |
| 7,555,340 | B2 | 6/2009 | Dong et al. |
| 7,558,628 | B2 | 7/2009 | Yonce et al. |
| 2001/0012953 | A1 | 8/2001 | Molin et al. |
| 2001/0049542 | A1 | 12/2001 | Florio et al. |
| 2001/0049543 | A1 | 12/2001 | Kroll |
| 2002/0077559 | A1 | 6/2002 | Ding et al. |
| 2002/0095183 | A1 | 7/2002 | Casset et al. |
| 2002/0133198 | A1 | 9/2002 | Kramer et al. |
| 2002/0161307 | A1 | 10/2002 | Yu et al. |
| 2002/0193696 | A1 | 12/2002 | Hsu et al. |
| 2003/0083700 | A1 | 5/2003 | Hill |
| 2003/0083710 | A1 | 5/2003 | Ternes et al. |
| 2003/0083711 | A1 | 5/2003 | Yonce et al. |
| 2003/0144702 | A1 | 7/2003 | Yu et al. |
| 2003/0144703 | A1 | 7/2003 | Yu et al. |
| 2003/0204212 | A1 | 10/2003 | Burnes et al. |
| 2004/0088018 | A1 | 5/2004 | Sawchuk |
| 2004/0158165 | A1 | 8/2004 | Yonce et al. |
| 2004/0158293 | A1 | 8/2004 | Yonce et al. |
| 2004/0215249 | A1 | 10/2004 | Corbucci |
| 2004/0215252 | A1 | 10/2004 | Verbeek et al. |
| 2005/0038478 | A1 | 2/2005 | Klepfer et al. |
| 2005/0209649 | A1 | 9/2005 | Ferek-petric |
| 2005/0209650 | A1 | 9/2005 | Van Gelder et al. |
| 2006/0224198 | A1 | 10/2006 | Dong et al. |
| 2006/0241706 | A1 | 10/2006 | Yonce et al. |
| 2007/0162082 | A1 | 7/2007 | Ternes et al. |
| 2007/0219593 | A1 | 9/2007 | Yonce et al. |
| 2009/0270937 | A1 | 10/2009 | Yonce et al. |

FOREIGN PATENT DOCUMENTS

| | | |
|---|---|---|
| EP | 1155711 | 11/2001 |
| WO | WO-03/020366 A1 | 3/2003 |
| WO | WO-03/022148 A1 | 3/2003 |
| WO | WO-03/037428 A2 | 5/2003 |
| WO | WO-2004/026398 A1 | 4/2004 |
| WO | WO-2005/053792 A1 | 6/2005 |

OTHER PUBLICATIONS

"U.S. Appl. No. 10/003,718, Response filed Apr. 12, 2004 to Restriction Requirement mailed Mar. 11, 2004", 10 pgs.

"U.S. Appl. No. 10/003,718, Final Office Action mailed Sep. 13, 2005", 6 pgs.

"U.S. Appl. No. 10/003,718, Non Final Office Action mailed Mar. 22, 2006", 5 pgs.

"U.S. Appl. No. 10/003,718, Non-Final Office Action mailed Sep. 30, 2004", 5 pgs.

"U.S. Appl. No. 10/003,718, Notice of Allowance mailed Sep. 27, 2006", 6 pgs.

"U.S. Appl. No. 10/003,718, Response filed Jan. 13, 2006 to Final Office Action mailed Sep. 13, 2005", 9 pgs.

"U.S. Appl. No. 10/003,718, Response filed Jul. 24, 2006 to Non-Final Office Action mailed Mar. 22, 2006", 11 pgs.

"U.S. Appl. No. 10/003,718, Response filed Dec. 30, 2004 to Non-Final Office Action mailed Sep. 30, 2004", 10 pgs.

"U.S. Appl. No. 10/003,718, Restriction Requirement mailed Mar. 11, 2004", 5 pgs.

"U.S. Appl. No. 10/251,629, Appeal Brief filed Oct. 23, 2006", 24 pgs.

"U.S. Appl. No. 10/251,629, Restriction Requirement mailed Jun. 28, 2005", 5 pgs.

"U.S. Appl. No. 10/251,629, Final Office Action mailed Mar. 22, 2006", 9 pgs.

"U.S. Appl. No. 10/251,629, Non-Final Office Action mailed Oct. 13, 2005", 7 pgs.

"U.S. Appl. No. 10/251,629, Notice of Allowance mailed Feb. 20, 2007", 4 pgs.

"U.S. Appl. No. 10/251,629, Response filed Feb. 13, 2006 to Non-Final Office Action mailed Oct. 13, 2005", 11 pgs.

"U.S. Appl. No. 10/251,629, Response filed Jul. 28, 2005 to Restriction Requirement mailed Jun. 28, 2005", 9 pgs.

"U.S. Appl. No. 10/723,254, Advisory Action mailed Jan. 9, 2007", 3 pgs.

"U.S. Appl. No. 10/723,254, Appeal Brief mailed filed Jan. 21, 2009", 19 pgs.

"U.S. Appl. No. 10/723,254, Final Office Action mailed Jul. 15, 2008", 7 pgs.

"U.S. Appl. No. 10/723,254, Final Office Action mailed Oct. 6, 2006", 7 pgs.

"U.S. Appl. No. 10/723,254, Final Office Action mailed Oct. 9, 2007", 7 pgs.

"U.S. Appl. No. 10/723,254, Non-Final Office Action mailed Jan. 7, 2008", 8 pgs.

"U.S. Appl. No. 10/723,254, Non-Final Office Action mailed Feb. 16, 2007", 6 pgs.

"U.S. Appl. No. 10/723,254, Non-Final Office Action mailed Apr. 26, 2006", 6 pgs.

"U.S. Appl. No. 10/723,254, Response filed Jul. 16, 2007 to Non-Final Office Action mailed Feb. 16, 2007", 8 pgs.

"U.S. Appl. No. 10/723,254, Response filed Jul. 26, 2006 to Non-Final Office Action mailed Apr. 26, 2006", 7 pgs.

"U.S. Appl. No. 10/723,254, Response filed Oct. 30, 2007 to Final Office Action mailed Oct. 9, 2007", 8 pgs.

"U.S. Appl. No. 10/723,254, Response filed Dec. 6, 2006 to Final Office Action mailed Oct. 6, 2006", 6 pgs.

"U.S. Appl. No. 10/723,254, Response filed Apr. 7, 2008 to Non-Final Office Action mailed Jan. 7, 2008", 8 pgs.

"U.S. Appl. No. 10/723,255, Non Final Office Action mailed Nov. 30, 2005", 5 pgs.

"U.S. Appl. No. 10/723,255, Notice of Allowance mailed Mar. 22, 2006", 4 pgs.

"U.S. Appl. No. 10/723,255, Notice of Allowance mailed Jun. 2, 2005", 6 pgs.

"U.S. Appl. No. 10/723,255, Response filed Feb. 28, 2006 to Non-Final Office Action mailed Nov. 30, 2005", 8 pgs.

"U.S. Appl. No. 10/744,911, Response filed Jun. 30, 2006 to Non-Final Office Action mailed Mar. 2, 2006", 12 pgs.

"U.S. Appl. No. 10/744,911, Final Office Action mailed Dec. 15, 2006", 7 pgs.

"U.S. Appl. No. 10/744,911, Non-Final office action mailed Mar. 2, 2006", 8 pgs.

"U.S. Appl. No. 10/744,911, Notice of Allowance mailed Jan. 25, 2008", 6 pgs.

"U.S. Appl. No. 10/744,911, Response filed Mar. 15, 2007 to Final Office Action mailed Dec. 15, 2006", 13 pgs.

"U.S. Appl. No. 11/097,460, Non-Final Office Action with Restriction Requirement mailed Apr. 17, 2008", 15 pgs.

"U.S. Appl. No. 11/097,460, Notice of Allowance mailed Mar. 6, 2009", 6 pgs.

"U.S. Appl. No. 11/097,460, Notice of Allowance mailed Nov. 10, 2008", 7 pgs.

"U.S. Appl. No. 11/097,460, Response filed Jul. 17, 2008 to Non-Final Office Action mailed Apr. 17, 2008", 12 pgs.

"U.S. Appl. No. 11/456,485, Notice of Allowance mailed Mar. 9, 2009", 6 pgs.

"U.S. Appl. No. 11/456,485, Notice of Allowance mailed Nov. 10, 2008", 12 pgs.

"International Application Serial No. PCT/US03/29181, International Search Report mailed Jan. 28, 2004", 7 pgs.

"Japanese Application Serial No. 2004-537888, Notice of Reasons for Rejection mailed Aug. 31, 2009", (w/ Engliish Translation), 8 pgs.

Ternes, David, et al., "Method and Apparatus for Capture Verification and Threshold Determination", U.S. Appl. No. 11/620,901, filed Jan. 8, 2007, 25 pgs.

"U.S. Appl. No. 11/620,901, Response and Preliminary Amendment filed Dec. 28, 2009 to Restriction Requirement mailed Nov. 27, 2009", 9 pgs.

"U.S. Appl. No. 11/620,901, Final Office Action mailed Oct. 7, 2010", 8 pgs.

"U.S. Appl. No. 11/620,901, Non-Final Office Action mailed Mar. 22, 2010", 7 pgs.

"U.S. Appl. No. 11/620,901, Response filed Jul. 21, 2010 to Non-Final Office Action mailed Mar. 22, 2010", 8 pgs.

"U.S. Appl. No. 11/754,496 Non-Final Office Action mailed Oct. 7, 2010", 6 pgs.

"European Application Serial No. 03749727.8, Response filed Sep. 10, 2010 to Office Action mailed Mar. 9, 2010", 10 pgs.

"European Application Serial No. 03749727.8, Office Action mailed Mar. 9, 2010", 5 pgs.

"Japanese Application Serial No. 2004-537888, Amended Claims filed Nov. 27, 2009", (w/ English Translation of Amended Claims), 17 pgs.

"Japanese Application Serial No. 2004-537888, Final Office Action mailed May 21, 2010", (w/ English Translation), 5 pgs.

"Japanese Application Serial No. 2004-537888, Response filed Sep. 16, 2010 to Final Office Action mailed May 21, 2010", 14 pgs.

ELECTROGRAM MORPHOLOGY-BASED CRT OPTIMIZATION

CROSS REFERENCE TO RELATED APPLICATION

This application is a continuation of U.S. application Ser. No. 11/097,460, filed Apr. 1, 2005, now issued as U.S. Pat. No. 7,555,340, which is hereby incorporated by reference in its entirety.

FIELD OF THE INVENTION

This patent application pertains to methods and apparatus for the treatment of cardiac disease. In particular, it relates to methods and apparatus for improving cardiac function with resynchronization therapy.

BACKGROUND

Implantable devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate atrial or ventricular fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised pumping performance.

Heart failure refers to a clinical syndrome in which an abnormality of cardiac function causes a below normal stroke volume that can fall below a level adequate to meet the metabolic demand of peripheral tissues. It usually presents as congestive heart failure (CHF) due to the accompanying venous and pulmonary congestion. Heart failure can be due to a variety of etiologies with ischemic heart disease being the most common. Some heart failure patients suffer from some degree of AV block or are chronotropically deficient such that their cardiac output can be improved with conventional bradycardia pacing. Such pacing, however, may result in some degree of uncoordination in atrial and/or ventricular contractions because pacing excitation from a single pacing site is spread throughout the myocardium only via the much slower conducting muscle fibers of either the atria or the ventricles, and not the specialized conduction pathways. Most pacemaker patients can still maintain more than adequate cardiac output with artificial pacing, but the diminishment in pumping efficiency may be significant in a heart failure patient whose cardiac output is already compromised. Intraventricular and/or interventricular conduction defects are also commonly found in heart failure patients and can contribute to cardiac dysfunction by causing unsynchronized contractions during intrinsic beats.

In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Currently, a most common form of CRT applies stimulation pulses in either a left ventricle-only pacing mode or a biventricular pacing mode, where the pace or paces are delivered after a programmed atrio-ventricular (AV) delay interval with respect to the detection an intrinsic atrial contraction or delivery of an atrial pace. In the case of biventricular pacing, a first pace to one ventricle is delivered after the AV delay interval, and a second pace to the contralateral ventricle is then delivered after a specified ventriculo-ventricular (VV) delay interval with respect to the first pace. Appropriate specification of these parameters is necessary in order to achieve the desired optimum coordination between the atria and the ventricles and within the ventricles.

SUMMARY

The present disclosure relates to methods and apparatus for delivering cardiac resynchronization therapy (CRT) in which an evoked response electrogram is recorded during one or more cardiac cycles and used to determine an optimum AV delay interval and/or VV delay interval for delivering CRT and/or to monitor the effectiveness of such therapy. The optimum AV delay interval may be regarded as one which results in a coincidence of paced and intrinsic cardiac activity in a patient with intact native AV conduction. In a particular embodiment for optimizing the AV delay interval, an evoked response electrogram is recorded during a paced cardiac cycle using a short AV delay interval such that no intrinsic activation of the ventricles occurs. The AV delay interval is then incremented during subsequent cardiac cycles until intrinsic activation occurs, as revealed by a morphology analysis of the recorded evoked response electrogram. Intrinsic activation may be detected when the morphology of the evoked response electrograms recorded with the short and incremented AV delay intervals differs by a specified amount. In another embodiment, the VV delay interval is also optimized by testing a range of VV delay values, where the optimum AV and VV delay interval values are selected as those which produce the desired morphology in the evoked response waveform.

DETAILED DESCRIPTION

Figure 1:
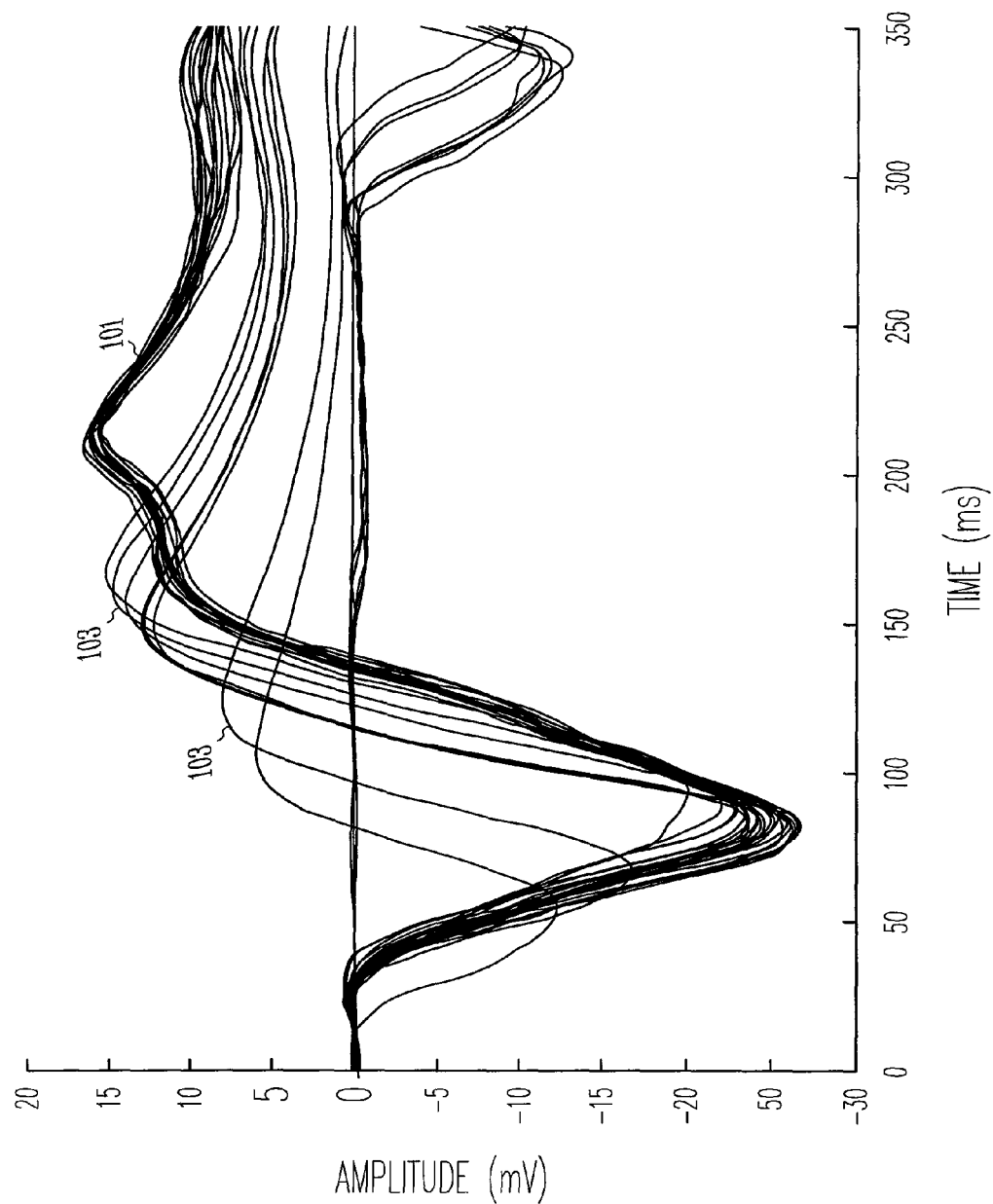
FIG. 1 shows an example of evoked response electrograms showing paced activation only and fusion of paced and intrinsic activation.

As described above, cardiac resynchronization therapy is pacing stimulation applied to one or more heart chambers in a manner that compensates for conduction delays. Ventricular resynchronization pacing is useful in treating heart failure in patients with interventricular or intraventricular conduction defects because, although not directly inotropic, resynchronization results in a more coordinated contraction of the ventricles with improved pumping efficiency and increased cardiac output. Ventricular resynchronization can be achieved in certain patients by pacing at a single unconventional site, such as the left ventricle instead of the right ventricle in patients with left ventricular conduction defects. Resynchronization pacing may also involve biventricular pacing with the paces to right and left ventricles delivered either simultaneously or sequentially, with the interval between the paces termed the VV delay (VVD) interval (also sometimes referred to as the LV offset (LVO) interval or biventricular offset (BVO) interval). The VV delay interval may be zero in order to pace both ventricles simultaneously, or non-zero in order to pace the left and right ventricles sequentially. As the term is used herein, a negative VVD refers to pacing the left ventricle before the right, while a positive VVD refers to pacing the right ventricle first.

Cardiac resynchronization therapy is most conveniently delivered in conjunction with a bradycardia pacing mode. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. In atrial tracking and AV sequential pacing modes, another ventricular escape interval is defined between atrial and ventricular events, referred to as the AV delay (AVD) interval, where a ventricular pacing pulse is delivered upon expiration of the AV delay interval if no ventricular sense occurs before. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing are commonly combined so that an AVD interval starts with either an atrial pace or sense. As the term is used herein for biventricular pacing, the AVD interval refers to the interval between an atrial event (i.e., a pace or sense in one of the atria, usually the right atrium) and the first ventricular pace which pre-excites one of the ventricles, and the pacing instant for the non-pre-excited ventricle is specified by the VVD interval so that it is paced at an interval AVD+VVD after the atrial event. With either biventricular or left ventricle-only pacing, the AVD interval may be the same or different depending upon whether it is initiated by an atrial sense or pace (i.e., in atrial tracking and AV sequential pacing modes, respectively). A common way of implementing biventricular pacing or left ventricle-only pacing is to base the timing upon only right ventricular activity so that ventricular escape intervals are reset or stopped by right ventricular senses.

For optimum hemodynamic performance, it is desirable to deliver ventricular pacing, whether for resynchronization pacing or conventional bradycardia pacing, in an atrial tracking and/or AV sequential pacing mode in order to maintain the function of the atria in pre-loading the ventricles (sometimes referred to atrio-ventricular synchrony). Since the objective of CRT is to improve a patient's cardiac pumping function, it is therefore normally delivered in an atrial-tracking and/or AV sequential mode and requires specification of an AVD interval (and, in the case of biventricular pacing, a VVD interval) which, ideally, results in the ventricles being synchronized during systole after being optimally preloaded during atrial systole. That is, both optimal interventricular synchrony and optimal atrio-ventricular synchrony are achieved.

Cardiac resynchronization therapy is most commonly applied in the treatment of patients with heart failure due to left ventricular dysfunction which is either caused by or contributed to by left ventricular conduction abnormalities such as left bundle branch block. (More rarely, some patients have a right ventricular conduction deficit such as right bundle branch block and require pre-excitation of the right ventricle in order achieve synchronization of their ventricular contractions.) In patients with a left ventricular conduction deficit, the left ventricle or parts of the left ventricle contract later than normal during systole which thereby impairs pumping efficiency. In order to resynchronize ventricular contractions in such patients, pacing therapy is applied such that the left ventricle or a portion of the left ventricle is pre-excited relative to when it would become depolarized in an intrinsic contraction. Optimal pre-excitation of the left ventricle in a given patient may be obtained with biventricular pacing or with left ventricular-only pacing by pre-exciting the left ventricle with a pace delivered to the left ventricle which excites the left ventricular free wall. The desired situation is simultaneous contraction of the left ventricular free wall and ventricular septum (septum-free wall fusion). The excitation of the ventricular septum may be a result of either intrinsic activation from the AV node or a pace delivered to the right ventricle. If intrinsic AV conduction to the right ventricle is normal, intrinsic activation of the ventricular septum occurs at an interval following an atrial contraction which produces optimal pre-loading of the ventricles during atrial systole. Therefore, in a patient with normal intrinsic AV conduction to the right ventricle but with a left ventricular conduction deficit, the hemodynamically optimum AVD interval for pre-exciting the left ventricle is one which results in the left ventricular free wall contracting due to the pace at the same time that the ventricular septum is contracting due to intrinsic activation. This situation may be brought about by pre-exciting the left ventricle at the optimum AVD interval with either left ventricle-only or biventricular pacing. In the latter case, depending upon the implementation, the right ventricular pace scheduled to occur at the VVD interval following expiration of the AVD interval may either be inhibited by the intrinsic right ventricular activation, occur coincidently with the right ventricular activation, or occur after intrinsic right ventricular activation during the refractory period.

In the case of a patient without intact intrinsic AV conduction, left ventricle-only pacing would produce a ventricular contraction in which depolarization spreads only from the left ventricular pacing site. It may therefore be desirable to deliver paces to both ventricles in a biventricular pacing mode in order to produce a more hemodynamically effective contraction. The minimum pacing rate would normally then be set to a value which results in only paced cycles. That is, any intrinsic activation due to an idioventricular rhythm would occur at too slow a rate to inhibit paces. The AV delay and VV delay intervals are then set to values which provide atrio-ventricular and interventricular synchrony. If, however, the patient does not have complete AV block, such that intrinsic activation of either ventricle may occur intermittently, it may be desirable to utilize biventricular pacing and to set the AV delay and VV delay intervals to values which produce fusion beats when intrinsic conduction to the ventricles occurs. For example, in a patient with a left ventricular conduction deficit and intermittent AV block to the right ventricle, pre-excitation of the left ventricle with an optimum AV delay intervals would produce a fusion beat when intrinsic conduction to the right ventricle occurs which results in the left ventricular free wall contracting due to the pace at the same time that the ventricular septum is contracting due to intrinsic activation. The optimum VV delay in this case would then be a value long enough to so that the right ventricular pace subsequent to the left ventricular pace is inhibited by the intrinsic right ventricular activation (or is delivered when the right ventricle is refractory) but short enough to produce a hemodynamically effect beat when no intrinsic AV conduction to the right ventricle occurs.

As discussed above, in a patient with normal intrinsic AV conduction to the right ventricle and a left ventricular conduction deficit, the desired result of CRT is a fusion beat such that the left ventricular pace causes contraction of the left ventricular free wall at the same time intrinsic conduction from the AV node causes contraction of the ventricular septum. Such a fusion beat may be recognized in an evoked response electrogram. An electrogram is a signal showing the amplitude and time course of cardiac depolarization and repolarization as recorded by either internal or external electrodes, the latter referred to as a surface EKG. An evoked response electrogram is one recorded during a paced cardiac cycle. Since the depolarization and repolarization patterns in the ventricles are different for paced and intrinsic activation, electrograms recorded during paced, intrinsically activated, and fusion beats are morphologically distinguishable. FIG. 1 shows a representation of an evoked response electrograms 101 recorded during a cardiac cycle when both ventricles are activated by a pace delivered to the left ventricle with no intrinsic activation, i.e., a purely paced beat. Purely paced beats can occur with left ventricle-only pacing when the left ventricular pace is delivered early enough that the depolarization spreads to and excites the right ventricle before intrinsic activation occurs. In the case of biventricular pacing with a negative VV delay interval, an evoked response electrogram may represent a purely paced beat or a fusion beat in which the left ventricle is paced but the right ventricle is intrinsically activated with the right ventricular pace being inhibited. A purely paced beat in this situation may occur with spread of excitation from the left ventricular pace or by both the right ventricular and left ventricular paces capturing the heart before intrinsic activation. The desired optimal situation for treating left ventricular conduction disorders with CRT in patients with at least some degree of normal AV conduction, however, is a fusion beat where the left ventricle is excited by the left ventricular pace while the right ventricle is intrinsically activated by conduction from the AV node. Such a fusion beat is represented by evoked response electrograms 103 for the case of left ventricle-only pacing. Since the morphologies of electrograms 101 and 103 are different, it is possible to distinguish between purely paced beats and fusion beats by comparing the electrograms or particular features derived therefrom.

The difference in morphologies of evoked response electrograms may be employed by a system to compute optimal settings for the AV delay and VV delay parameters for resynchronization pacing, i.e., intervals which result in the desired fusion beats. An exemplary computation method for determining an optimum AV delay interval is as follows. First, an evoked response electrogram is recorded during a cardiac cycle in which a ventricular resynchronization pace (either a biventricular or left ventricle-only pace) is delivered at an AVD interval selected to be short enough so that paced excitation of both ventricles occurs before intrinsic activation. The short AVD electrogram, or an average of such electrograms, may then be used as a purely paced reference waveform with which to compare electrograms recorded during subsequent paced cycles with longer AVD intervals to determine when a fusion beat occurs. The AVD interval can thus be gradually incremented until a fusion beat occurs, at which point the optimum AV delay interval is found. A fusion beat may be detected when there is a sufficient change in the evoked response electrogram as compared to the purely paced reference waveform. Whether a sufficient change has occurred may be determined by cross-correlating the evoked response electrogram with the purely paced reference waveform and comparing the resulting correlation coefficient with a predetermined threshold value. Alternatively, a particular feature may be extracted from both the evoked response electrogram waveform and the reference waveform, with the difference between the extracted features then compared to a threshold value. Examples of such features which may be extracted and compared include peak amplitudes, time intervals between particular identifiable points in the electrogram waveforms, and computed functions of the electrogram waveforms.

In an alternative embodiment, an evoked response electrogram is recorded during a cardiac cycle in which a ventricular resynchronization pace (either a biventricular or left ventricle-only pace) is delivered at an AVD interval selected to be long enough so that both ventricles are intrinsically activated. The long AVD electrogram, or an average of such electrograms, may then be used as an intrinsic reference waveform with which to compare electrograms recorded during subsequent paced cycles with shorter AVD intervals to determine when a fusion beat occurs. The AVD interval is gradually decremented until a fusion beat occurs, at which point the optimum AV delay interval is found. Similar to the previous embodiment, a fusion beat is detected when there is a sufficient change in the evoked response electrogram as compared to the intrinsic reference waveform.

A separate optimum AVD interval may be computed as described above for AVD intervals initiated by an atrial pace and for AVD intervals initiated by an atrial sense. Also, separate optimum AVD intervals may be computed for different atrial rates in order to track the physiological varying of the intrinsic AV interval with heart rate. The atrial rate in a normal individual increases in response to increased metabolic demand or emotional excitement due to hormonal and neural influences, the latter being increased sympathetic discharge relative to parasympathetic discharge. The neural and hormonal influences responsible for the increased heart rate also increase the force of cardiac contractions and decrease the intrinsic AV interval since the ventricles need to be filled more rapidly during a shorter diastole if cardiac output is to be increased. Separate optimum AVD intervals may also be computed for atrial rates as a result of atrial pacing. The optimum AVD interval may also vary as a function of pacing pulse energy (i.e., pulse amplitude and/or pulse width). An empirically derived look-up table or other mapping function can be employed by the implantable device to map particular atrial rates and/or pacing pulse energies to different programmed optimum AVD intervals.

In the case of biventricular pacing, an optimum VV delay interval for producing fusion beats may also determined by varying the VV delay interval as evoked response electrograms are recorded and comparing the evoked response electrogram with a reference electrogram to determine when a fusion beat occurs. In one embodiment, an optimum AV delay interval is first determined by the techniques described above using left ventricle-only pacing or biventricular pacing with a long VV delay. Next, biventricular pacing is delivered with a short VV delay so as to produce beats with biventricular capture which can be used as a purely paced reference electrogram waveform. The VV delay is then gradually lengthened until a fusion beat is detected by comparing the evoked response electrogram with the reference waveform in the same manner as discussed earlier. At that point, the optimum VV delay interval is found. In an alternative embodiment, a long VV delay is used to generate a fusion beat reference. An initially long VV delay is then gradually shortened until sufficient change evidencing a purely paced beat occurs, at which point the optimum VV delay interval is found. In another embodiment, multiple sites of the left ventricle are pre-excited with pacing pulses delivered at separate VV delay intervals. Optimum VV delay intervals may be found for each of the multiple pacing sites using either the incremented or decremented VV delay interval approach as just described above.

The techniques for computing optimum AVD and VVD intervals as described above may be implemented in a number of different ways. In one implementation, a system for setting the pacing parameters includes an external programmer and an implantable device. The external programmer commands the implantable device to vary the AVD and/or VVD intervals as described while electrogram signals generated by the sensing channels of the implantable device are transmitted to the external programmer via a wireless telemetry link. The external programmer then computes the optimum AVD and/or VVD intervals by detecting fusion beats. In an automated system, the external programmer then automatically programs the implantable device with the computed optimum AVD and/or VVD interval value or values, while in a semi-automated system the external programmer presents the computed optimum values to a clinician in the form of a recommendation. An automated system may also be made up of the implantable device alone which is programmed to vary the AVD and/or VVD intervals, record evoked response electrograms in order to detect fusion beats, and then automatically set the AVD and/or VVD intervals to the determined optimum value or values. In another embodiment, which may be referred to as a manual system, the external programmer presents the recorded evoked response electrograms to a clinician for comparison and determination of the optimum AVD and/or VVD interval values. Unless otherwise specified, references to a system for computing or setting pacing parameters throughout this document should be taken to include any of the automated, semi-automated, or manual systems just described.

A description of an exemplary cardiac rhythm management device suitable for delivering CRT therapy and recording evoked response electrograms is set forth below. The techniques for optimizing and monitoring CRT performance discussed above may be implemented by appropriate programming of the device's controller.

1. Exemplary Device Description

Cardiac rhythm management devices such as pacemakers and ICDs are typically implanted subcutaneously on a patient's chest and have leads threaded intravenously into the heart to connect the device to electrodes used for sensing and delivery of electrical stimulation such as defibrillation shocks and pacing pulses. A programmable electronic controller causes the delivery of pacing pulses in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above the capture threshold must be delivered to the chamber.

Figure 2:
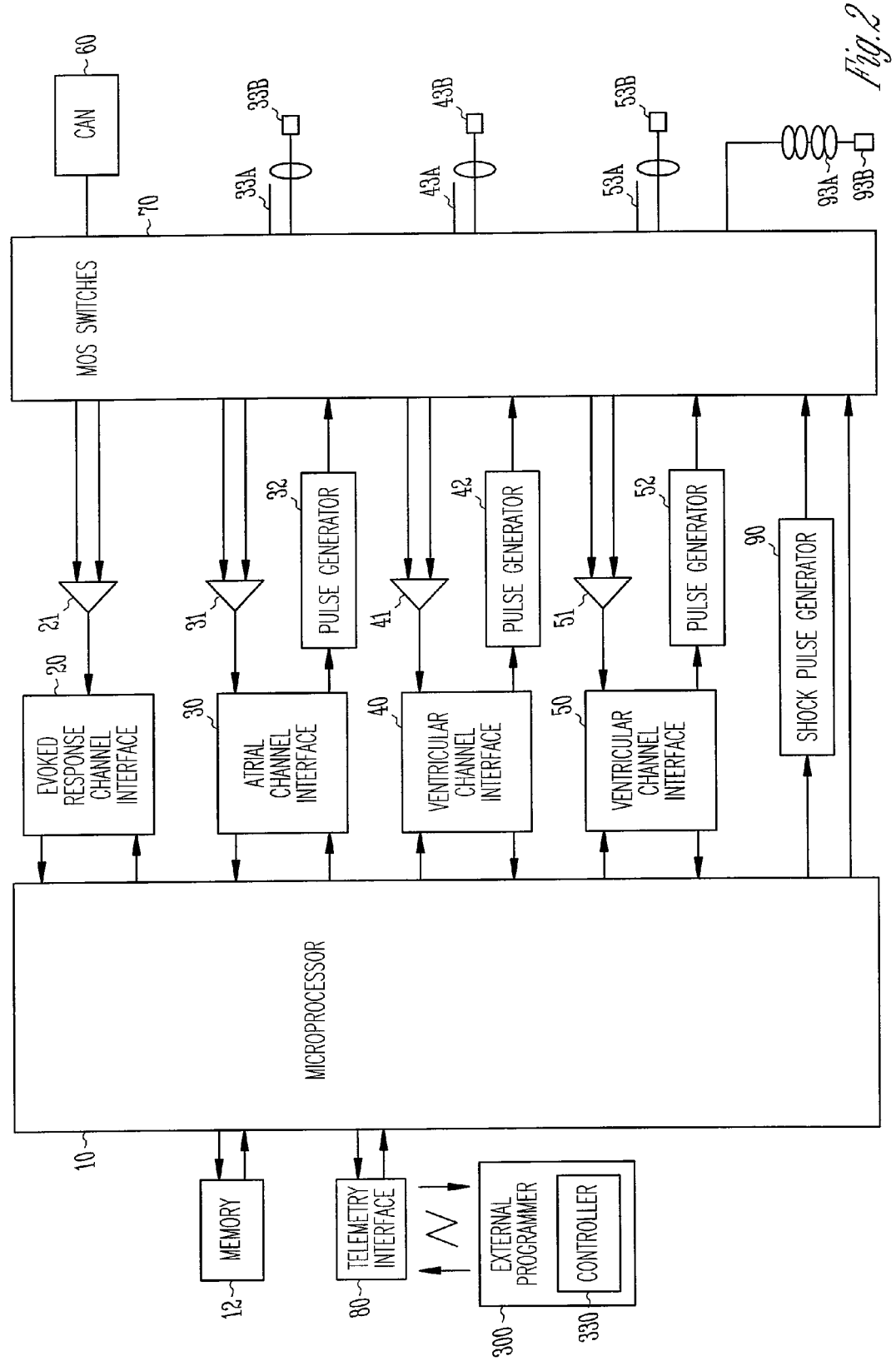
FIG. 2 is a system diagram of an exemplary CRT device.

A system diagram of an exemplary cardiac rhythm management device for delivering cardiac resynchronization therapy is illustrated in FIG. 2. The controller of the device is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the device in a number of programmed modes where a programmed mode defines how pacing pulses are output in response to sensed events and expiration of time intervals. A telemetry interface 80 is provided for communicating with an external programmer 300. The external programmer is a computerized device with a controller 330 that can interrogate the device and receive stored data as well as adjust various operating parameters.

The device has an atrial sensing/pacing channel comprising ring electrode 33a, tip electrode 33b, sense amplifier 31, pulse generator 32, and an atrial channel interface 30 which communicates bidirectionally with a port of microprocessor 10. The device also has two ventricular sensing/pacing channels that similarly include ring electrodes 43a and 53a, tip electrodes 43b and 53b, sense amplifiers 41 and 51, pulse generators 42 and 52, and ventricular channel interfaces 40 and 50. For each channel, the electrodes are connected to the pacemaker by a lead and used for both sensing and pacing. A MOS switching network 70 controlled by the microprocessor is used to switch the electrodes from the input of a sense amplifier to the output of a pulse generator. The device also includes a shock pulse generator 90 interfaced to the controller and a shock lead which incorporates a tip electrode 93b and a coil electrode 93a. Coil electrodes can be used to deliver pacing pulses but are designed especially for delivering cardioversion/defibrillation shocks. The shock lead would normally be disposed in the right ventricle (RV) so that sensing or pacing of the ventricles may be performed using tip electrode 93b and/or coil electrode 93a. A ventricular cardioversion/defibrillation shock may be delivered between coil 93a and the can 60 when fibrillation or other tachyarrhythmia is detected. The device also has an evoked response sensing channel that comprises an evoked response channel interface 20 and a sense amplifier 21 that has its differential inputs connected to a selected electrode and to the device housing or can 60 through the switching network 70. The evoked response sensing channel may be used to verify that a pacing pulse has achieved capture of the heart in a conventional manner or, as explained below, used to record an evoked response electrogram.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 10 controls the overall operation of the device in accordance with programmed instructions stored in memory. The sensing circuitry of the device generates atrial and ventricular sense signals when voltages sensed by the electrodes (i.e., electrograms) exceed a specified threshold. The controller then interprets sense signals from the sensing channels and controls the delivery of paces in accordance with a programmed pacing mode. The sense signals from any of the sensing channels of the pacemaker in FIG. 2 can be digitized and recorded by the controller to constitute an electrogram that can either be analyzed by the device itself or transmitted via the telemetry link 80 to the external programmer 300.

The electrical response of the heart to a pacing pulse is referred to as an evoked response. If the evoked response indicates that a propagating wave of depolarization has resulted from the pacing pulse, it evidences that the paced chamber has responded appropriately and contracted. As described herein, an electrogram can also be recorded of an evoked response to a pace and used to determine if a desired fusion beat has occurred. An evoked response sensing channel for recording an electrogram can be a sensing channel normally used for other purposes or can be a sensing channel dedicated to sensing evoked responses. In the embodiment illustrated in FIG. 2, a dedicated evoked response sensing channel is provided where the differential inputs of sensing amplifier 21 may be connected to a selected electrode and the can 60 by means of switch matrix 70. An electrogram signal for morphology analysis is preferably obtained from a unipolar electrode with a large surface area rather than a conventional bipolar sensing/pacing electrode. It is preferable for the evoked response sensing channel to employ unipolar sensing such that the sensing vector is between the unipolar electrode and the device housing or can (or another distantly disposed electrode or electrodes). A large unipolar electrode "sees" a larger volume of the myocardium, and changes in the depolarization pattern of the ventricles will be more readily reflected in an electrogram generated by the electrode during a ventricular beat. A convenient electrode for this purpose is the coil electrode that the device normally uses for delivering cardioversion/defibrillation shocks. An electrogram signal suitable for morphology analysis may also be obtained by switching the dedicated sensing channel to a subcutaneous electrode, referred to as a subcutaneous ECG channel. Since the switch matrix allows different sensing vectors to be used for the optimization of AV and VV delays, it is desirable to select the most desirable sensing vectors for a particular patient. One example selection method is to collect the electrograms from different sensing vectors at several different AV and VV delays, extract the features, and choose the vectors which produce the maximum difference as the desired vector.

2. Example Algorithm for Optimal Adjustment of Programmed AV Delay Interval

Figure 3:
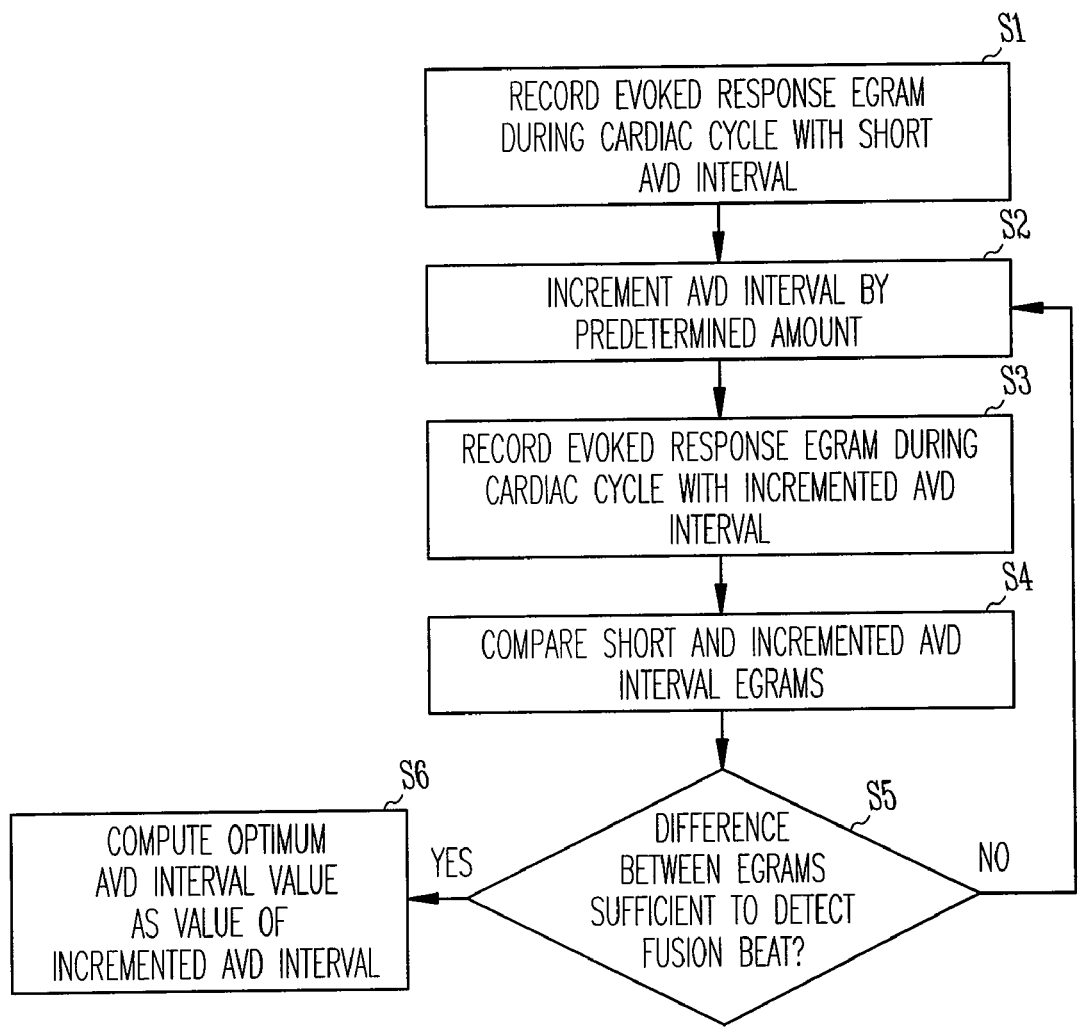
FIG. 3 illustrates an exemplary algorithm for computing an optimum AVD interval.

FIG. 3 illustrates an exemplary algorithm for determining an optimum AVD interval for delivering CRT to patients with intact native AV conduction. The algorithm may be performed by the controller of the implantable device, by an external programmer in communication with the implantable device, or by a clinician operating an external programmer. The implantable device is configured to deliver paces to both right and left ventricles or to the left ventricle only in accordance with a programmed pacing mode, such that the pace or paces are delivered after a programmed AV delay interval with respect to an atrial event. At step S1, an evoked response electrogram is recorded during a paced cardiac cycle with a short AV delay interval expected to be shorter than the patient's intrinsic atrioventricular interval. At step S2, the AV delay interval is incremented by a predetermined amount, and at step S3 another evoked response electrogram is recorded during a paced cardiac cycle with the incremented AV delay interval. At step S4, the evoked response electrograms recorded with the incremented and short AVD intervals are compared to determine if a sufficient difference is present to evidence occurrence of a fusion beat. Such a comparison may be performed by cross-correlating the two electrogram waveforms and computing a correlation coefficient CC:

$$CC = \frac{\sum_{i=1}^{n} x_i \cdot y_i}{\left[\sum_{i=1}^{n} x_i^2\right]^{1/2} \left[\sum_{i=1}^{n} y_i^2\right]^{1/2}}$$

where x is the short AVD electrogram, y is the incremented AVD electrogram, and n is the number of samples in the template. The value CC is then compared with a specified threshold value to determine if the difference between the two waveforms is sufficient to presume a fusion beat has occurred. Alternatively, specific features may be extracted from the two waveforms and compared. If the difference between the features extracted from each waveform exceeds a specified threshold value, a fusion beat may be presumed to have occurred. If the difference between the short AVD electrogram and the incremented AVD electrogram is sufficient, as tested for at step S5, the optimum AVD interval is determined to be the incremented AVD interval value at step S6. Otherwise, a return is made to step S2 where the AVD is incremented again by the predetermined amount until the evoked response electrogram recorded with the incremented AV delay interval differs from the evoked response electrogram recorded with the short AV delay interval by the specified threshold amount. The method may be performed to compute separate optimum AV delay interval depending upon whether the atrial event is an atrial sense or an atrial pace. The method may also be performed to determine optimum AV delay intervals at a plurality of different pacing rates, with the optimum AV delay intervals as determined at the plurality of pacing rates used to form a mapping function (e.g., a look-up table or linear function) which maps particular pacing rates to particular programmed AV delay intervals. The mapping function may then be used to automatically adjust the programmed AV delay interval as the pacing rate changes.

Although not as common, some patients have a right ventricular conduction deficit such as right bundle branch block and require pre-excitation of the right ventricle in order achieve synchronization of their ventricular contractions. The preceding discussions have focused primarily on the situation where one or more left ventricular sites are pre-excited with biventricular or left ventricle-only pacing. It should be appreciated that the techniques described herein could also be applied for optimally pre-exciting any late-contracting ventricular region, including in the right ventricle. In those cases, the right ventricle is pre-excited with an optimized AVD delay interval using either biventricular or right ventricle-only pacing.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device in a patient, comprising:
    delivering pacing therapy in accordance with a programmed pacing mode for pre-exciting one of the ventricles relative to the other ventricle, such that a pace to the pre-excited ventricle is delivered after a programmed AV delay interval with respect to an atrial event; and,
    determining an optimum AV delay interval by:
    recording an evoked response electrogram during a paced cardiac cycle with a short AV delay interval expected to be shorter than the patient's intrinsic atrioventricular interval to ensure that paced excitation of both ventricles occurs before intrinsic activation;
    incrementing the AV delay interval by a predetermined amount and recording an evoked response electrogram during a paced cardiac cycle with the incremented AV delay interval;
    comparing the evoked response electrograms recorded with the incremented and short AV delay intervals;
    continuing to increment the AV delay interval by the predetermined amount until the evoked response electrogram recorded with the incremented AV delay interval differs from the evoked response electrogram recorded with the short AV delay interval by a specified amount so as to indicate the occurrence of fusion beat that includes paced excitation of the pre-excited ventricle and intrinsic activation of the other ventricle; and,
    determining the optimum AV delay interval as the incremented AV delay interval used when the fusion beat occurs.

2. The method of claim 1 wherein the difference between the evoked response electrograms recorded with the short and incremented AV delay intervals is determined by performing a cross-correlation between the two electrograms and comparing a resulting cross-correlation coefficient to a specified threshold value.

3. The method of claim 1 wherein the difference between the evoked response electrograms recorded with the short and incremented AV delay intervals is determined by extracting a feature from each of the two electrograms and comparing a difference between the extracted features with a specified threshold value.

4. The method of claim 1 further comprising determining optimum AV delay intervals at a plurality of different pacing pulse energies.

5. The method of claim 1 further comprising determining optimum AV delay intervals at a plurality of different atrial rates.

6. The method of claim 5 further comprising:
    using the optimum AV delay intervals as determined at the plurality of atrial rates to form a mapping function which maps particular atrial rates to particular programmed AV delay intervals; and,
    automatically adjusting the programmed AV delay interval according to the mapping function as the atrial rate changes.

7. The method of claim 1 further comprising determining a separate optimum AV delay interval depending upon whether the atrial event is an atrial sense or an atrial pace.

8. The method of claim 1 further comprising determining an optimum VV delay interval for biventricular pacing by:
    recording an evoked response electrogram during a biventricular paced cardiac cycle with the determined optimum AV delay interval with a short VV delay interval expected to be short enough to produce biventricular capture;
    incrementing the VV delay interval by a predetermined amount and recording an evoked response electrogram during a paced cardiac cycle with the incremented VV delay interval;
    comparing the evoked response electrograms recorded with the incremented and short VV delay intervals; and,
    continuing to increment the VV delay interval by the predetermined amount until the evoked response electrogram recorded with the incremented VV delay interval differs from the evoked response electrogram recorded with the short VV delay interval by a specified amount.

9. The method of claim 8 further comprising determining optimum VV delay intervals for multiple pacing sites in the left ventricle.

10. The method of claim 1 further comprising selecting a sensing vector for generating evoked response electrograms which produces the greatest morphology difference between electrograms of fusion beats and electrograms of purely paced beats.

11. A cardiac rhythm management device, comprising:
    one or more pulse generators for delivering paces via pacing channels to both right and left ventricles;
    one or more sensing amplifiers for receiving an electrogram signal;
    a controller programmed to deliver pacing therapy in accordance with a programmed pacing mode for pre-exciting one of the ventricles relative to the other ventricle, such that a pace to the pre-excited ventricle is delivered after a programmed AV delay interval with respect to an atrial event;
    wherein the controller is programmed to determine an optimum AV delay interval by:
    recording an evoked response electrogram during a paced cardiac cycle with a short AV delay interval which is expected to be shorter than the patient's intrinsic atrioventricular interval;
    incrementing the AV delay interval by a predetermined amount and recording an evoked response electrogram during a paced cardiac cycle with the incremented AV delay interval;
    comparing the evoked response electrograms recorded with the incremented and short AV delay intervals;
    continuing to increment the AV delay interval by the predetermined amount until the evoked response electrogram recorded with the incremented AV delay interval differs from the evoked response electrogram recorded with the short AV delay interval by a specified amount so as to indicate the occurrence of fusion beat that includes paced excitation of the pre-excited ventricle and intrinsic activation of the other ventricle; and, determining the optimum AV delay interval as the incremented AV delay interval used when the fusion beat occurs.

12. The device of claim 11 wherein the difference between the evoked response electrograms recorded with the short and incremented AV delay intervals is determined by performing a cross-correlation between the two electrograms and comparing a resulting cross-correlation coefficient to a specified threshold value.

13. The device of claim 11 wherein the difference between the evoked response electrograms recorded with the short and incremented AV delay intervals is determined by extracting a feature from each of the two electrograms and comparing a difference between the extracted features with a specified threshold value.

14. The device of claim 11 wherein the controller is further programmed to determine optimum AV delay intervals at a plurality of different pacing pulse energies.

15. The device of claim 11 wherein the controller is further programmed to determine optimum AV delay intervals at a plurality of different atrial rates.

16. The device of claim 15 wherein the controller is further programmed to:

use the optimum AV delay intervals as determined at the plurality of atrial rates to form a mapping function which maps particular atrial rates to particular programmed AV delay intervals; and, automatically adjust the programmed AV delay interval according to the mapping function as the atrial rate changes.

17. The device of claim 11 wherein the controller is further programmed to determine a separate optimum AV delay interval depending upon whether the atrial event is an atrial sense or an atrial pace.

18. The device of claim 11 wherein the controller is further programmed to determine an optimum VV delay interval for biventricular pacing by:

recording an evoked response electrogram during a biventricular paced cardiac cycle with the determined optimum AV delay interval with a short VV delay interval expected to be short enough to produce biventricular capture;

incrementing the VV delay interval by a predetermined amount and recording an evoked response electrogram during a paced cardiac cycle with the incremented VV delay interval;

comparing the evoked response electrograms recorded with the incremented and short VV delay intervals; and, continuing to increment the VV delay interval by the predetermined amount until the evoked response electrogram recorded with the incremented VV delay interval differs from the evoked response electrogram recorded with the short VV delay interval by a specified amount.

19. The device of claim 18 wherein the controller is further programmed to determine optimum VV delay intervals for multiple pacing sites in the left ventricle.

20. The device of claim 11 wherein the controller is further programmed to select a sensing vector for generating evoked response electrograms which produces the greatest morphology difference between electrograms of fusion beats and electrograms of purely paced beats.

* * * * *